(12) United States Patent
Nazarifar et al.

(10) Patent No.: US 7,896,839 B2
(45) Date of Patent: Mar. 1, 2011

(54) SURGICAL CASSETTE FOR INTRAOCULAR PRESSURE CONTROL

(75) Inventors: Nader Nazarifar, Laguna Niguel, CA (US); Mark A. Hopkins, Mission Viejo, CA (US); Shawn X. Gao, Irvine, CA (US); Frederick M. Reed, Cypress, CA (US); John C. Huculak, Mission Viejo, CA (US); Roger D. Thomas, Tustin, CA (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 12/750,787

(22) Filed: Mar. 31, 2010

(65) Prior Publication Data

US 2010/0228199 A1 Sep. 9, 2010

Related U.S. Application Data

(62) Division of application No. 11/237,568, filed on Sep. 28, 2005, now Pat. No. 7,713,237.

(51) Int. Cl.
*A61M 1/00* (2006.01)

(52) U.S. Cl. ........................ 604/122; 604/118; 604/151

(58) Field of Classification Search ................... 604/30, 604/118, 122, 151, 890.1
See application file for complete search history.

(56) References Cited

U.S. PATENT DOCUMENTS

| | | | |
|---|---|---|---|
| 4,475,904 A | 10/1984 | Wang | |
| 4,713,051 A | 12/1987 | Steppe et al. | |
| 4,750,643 A | 6/1988 | Wortrich | |
| 4,758,238 A | 7/1988 | Sundblom et al. | |
| 4,813,927 A | 3/1989 | Morris et al. | |
| 4,832,685 A | 5/1989 | Haines | |
| 4,900,301 A | 2/1990 | Morris et al. | |
| 4,935,005 A | 6/1990 | Haines | |
| 4,963,131 A | 10/1990 | Wortrich | |
| 5,032,111 A | 7/1991 | Morris et al. | |
| 5,041,096 A | 8/1991 | Beuchat et al. | |
| 5,047,009 A | 9/1991 | Morris et al. | |
| 5,098,037 A | 3/1992 | Leffel et al. | |
| 5,106,366 A | 4/1992 | Steppe | |
| 5,163,900 A | 11/1992 | Wortrich | |
| 5,267,956 A | 12/1993 | Beuchat | |
| 5,282,787 A | 2/1994 | Wortrich | |
| D352,106 S | 11/1994 | Fanney et al. | |
| 5,364,342 A | 11/1994 | Beuchat et al. | |
| 5,499,969 A | 3/1996 | Beuchat et al. | |
| D375,553 S | 11/1996 | Creed et al. | |
| 5,582,601 A | 12/1996 | Wortrich et al. | |
| 5,588,815 A | 12/1996 | Zaleski, II | |
| 5,620,312 A | 4/1997 | Hyman et al. | |
| D380,550 S | 7/1997 | Dennewill et al. | |
| 5,643,203 A | 7/1997 | Beiser et al. | |

(Continued)

FOREIGN PATENT DOCUMENTS

CA 1068572 12/1979

(Continued)

*Primary Examiner*—Nicholas D Lucchesi
*Assistant Examiner*—Victoria P Campbell
(74) *Attorney, Agent, or Firm*—W. David Lee

(57) ABSTRACT

An improved surgical cassette for controlling intraocular pressure during ophthalmic surgery.

2 Claims, 3 Drawing Sheets

U.S. PATENT DOCUMENTS

| | | |
|---|---|---|
| 5,676,530 A | 10/1997 | Nazarifar |
| 5,676,650 A | 10/1997 | Grieshaber et al. |
| 5,700,240 A | 12/1997 | Barwick, Jr. et al. |
| 5,747,824 A | 5/1998 | Jung et al. |
| 5,800,396 A | 9/1998 | Fanney et al. |
| 5,865,764 A | 2/1999 | Moorhead |
| 5,897,524 A | 4/1999 | Wortrich et al. |
| 5,899,674 A | 5/1999 | Jung et al. |
| 6,059,544 A | 5/2000 | Jung et al. |
| 6,261,283 B1 | 7/2001 | Morgan et al. |
| 6,293,926 B1 | 9/2001 | Sorensen et al. |
| 6,561,999 B1 | 5/2003 | Nazarifar et al. |
| 6,572,349 B2 | 6/2003 | Sorensen et al. |
| 6,579,255 B2 | 6/2003 | Kadziauskas et al. |
| 6,632,214 B2 | 10/2003 | Morgan et al. |
| 6,740,074 B2 | 5/2004 | Morgan et al. |
| 6,824,525 B2 | 11/2004 | Nazarifar et al. |
| 6,902,542 B2 | 6/2005 | Gordon |
| 6,962,488 B2 | 11/2005 | Davis et al. |
| 2002/0019607 A1 | 2/2002 | Bui |
| 2002/0033370 A1 | 3/2002 | Bainbridge et al. |
| 2003/0050619 A1 | 3/2003 | Mooijman et al. |
| 2003/0108429 A1 | 6/2003 | Angelini et al. |
| 2003/0225363 A1 | 12/2003 | Gordon et al. |
| 2004/0116911 A1 | 6/2004 | Kadziauskas et al. |
| 2004/0253129 A1 | 12/2004 | Sorensen et al. |
| 2005/0065462 A1 | 3/2005 | Nazarifar et al. |

FOREIGN PATENT DOCUMENTS

| | | |
|---|---|---|
| CA | 1068574 | 12/1979 |
| DE | 18752574 A1 | 5/2000 |
| EP | 0776670 B1 | 9/2001 |
| EP | 1356835 A1 | 10/2003 |
| EP | 1612532 A1 | 4/2006 |
| WO | 03/047652 A1 | 6/2003 |
| WO | 03/047653 A1 | 6/2003 |
| WO | 03/047654 A1 | 6/2003 |

SURGICAL CASSETTE FOR INTRAOCULAR PRESSURE CONTROL

This application is a divisional of U.S. application Ser. No. 11/237,568 filed Sep. 28, 2005 now U.S. Pat. No. 7,713,237.

FIELD OF THE INVENTION

The present invention generally pertains to microsurgical systems and more particularly to controlling intraocular pressure in ophthalmic surgery.

DESCRIPTION OF THE RELATED ART

During small incision surgery, and particularly during ophthalmic surgery, small probes are inserted into the operative site to cut, remove, or otherwise manipulate tissue. During these surgical procedures, fluid is typically infused into the eye, and the infusion fluid and tissue are aspirated from the surgical site.

Maintaining an optimum intraocular pressure during ophthalmic surgery is currently problematic. When no aspiration is occurring, the pressure in the eye becomes the pressure of the fluid being infused into the eye. This pressure is typically referred to as the "dead head pressure". However, when aspiration is applied, the intraocular pressure drops dramatically from the dead head pressure due to all the pressure losses in the aspiration circuit associated with aspiration flow. Therefore, ophthalmic surgeons currently tolerate higher than desired dead head pressures to compensate for occasions when aspiration would otherwise lower the intraocular pressure to soft-eye conditions. Clinically, such over-pressurizing of the eye is not ideal.

Accordingly, a need continues to exist for improved apparatus for controlling intraocular pressure during ophthalmic surgery.

SUMMARY OF THE INVENTION

In one aspect, the present invention is a surgical cassette including a dual infusion chamber and first through fifth fluid lines. The dual infusion chamber has a first chamber not fluidly coupled to the second chamber. The first fluid line is fluidly coupled to the first chamber and is for providing an irrigating fluid to the first chamber. The second fluid line is fluidly coupled to the first chamber and is for providing the irrigating fluid to a surgical device. The third fluid line is fluidly coupled to the second chamber and is for providing the irrigating fluid to the second chamber. The fourth fluid line is fluidly coupled to the second chamber and is for providing the irrigating fluid to the surgical device. The fifth fluid line is fluidly coupled to one of the first chamber or the second chamber and is for providing the irrigating fluid to one of the first chamber or the second chamber.

BRIEF DESCRIPTION OF THE DRAWINGS

For a more complete understanding of the present invention, and for further objects and advantages thereof, reference is made to the following description taken in conjunction with the accompanying drawings, in which.

DETAILED DESCRIPTION OF THE PREFERRED EMBODIMENTS

Figure 1:
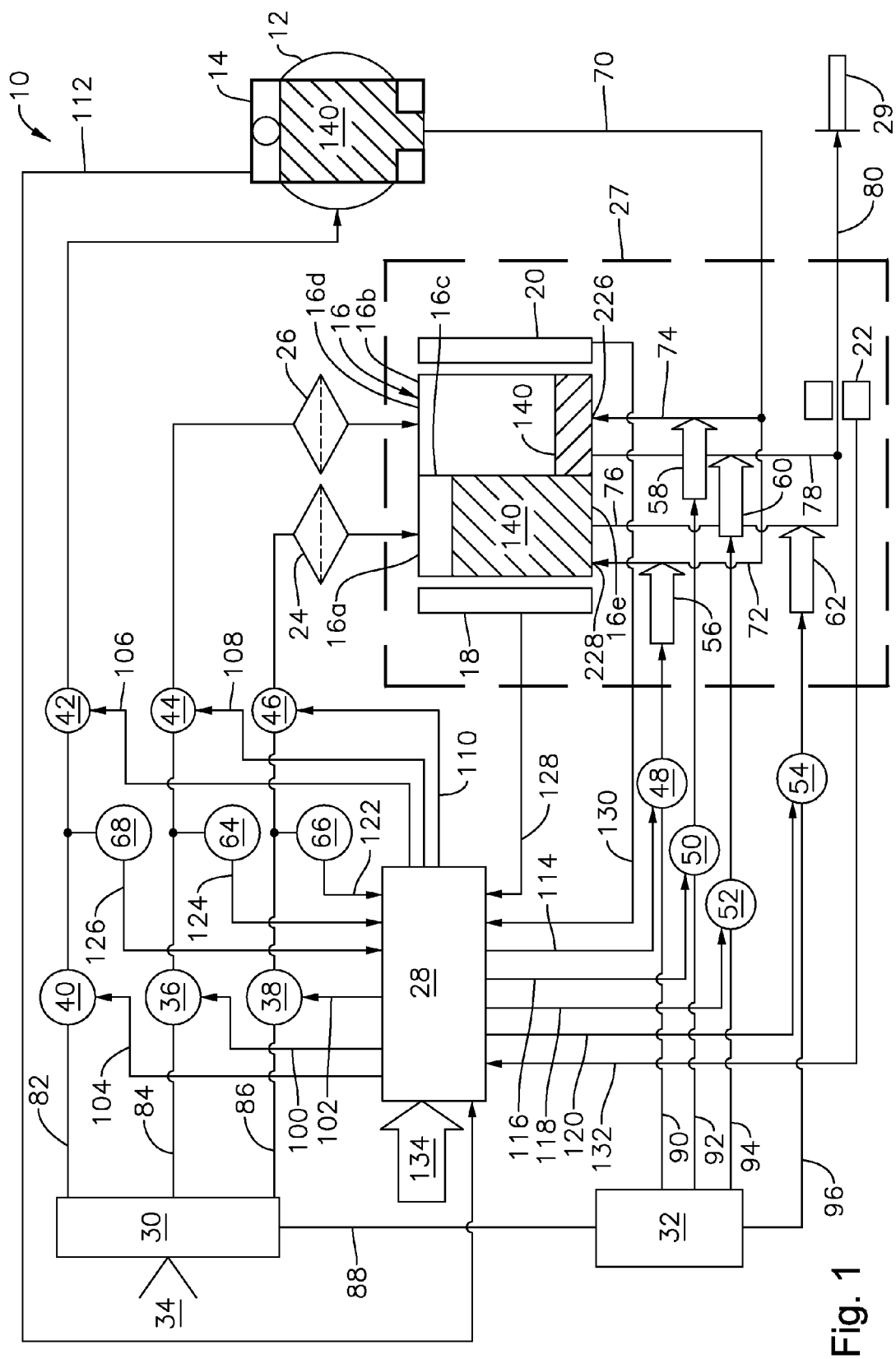
FIG. 1 is a schematic diagram illustrating infusion control in an ophthalmic microsurgical system.

The preferred embodiments of the present invention and their advantages are best understood by referring to FIGS. 1-4 of the drawings, like numerals being used for like and corresponding parts of the various drawings. As shown in FIG. 1, ophthalmic microsurgical system 10 includes a pressure cuff 12; an infusion source 14; a dual infusion chamber 16 having a chamber 16a and a chamber 16b; fluid level sensors 18 and 20; a flow sensor 22; filters 24 and 26; a surgical device 29; a computer or microprocessor 28; gas manifolds 30 and 32; a pressurized gas source 34; proportional solenoid valves 36, 38, and 40; "on/off" solenoid valves 42, 44, 46, 48, 50, 52, 54; actuators 56, 58, 60, and 62; and pressure transducers 64, 66, and 68. Dual infusion chamber 16; fluid level sensors 18 and 20; portions of infusion fluid lines 70, 72, 74, 76, 78, and 80; and portions of gas lines 84 and 86 are preferably disposed in a surgical cassette 27. Infusion source 14; dual infusion chamber 16; flow sensor 22; filters 24 and 26; and surgical device 29 are fluidly coupled via infusion fluid lines 70-80. Infusion source 14, dual infusion chamber 16, gas manifolds 30 and 32; pressurized gas source 34; and actuators 56, 58, 60, and 62 are fluidly coupled via gas lines 82, 84, 86, 88, 90, 92, 94, and 96. Infusion source 14; fluid level sensors 18-20; flow sensor 22; microprocessor 28; proportional solenoid valves 36-40; on/off solenoid valves 42-54; actuators 56-62; and pressure transducers 64-68 are electrically coupled via interfaces 100, 102, 104, 106, 108, 110, 112, 114, 116, 118, 120, 122, 124, 126, 128, 130, and 132.

Infusion source 14 is preferably a flexible infusion source. As shown best in FIGS. 3-4, dual infusion chamber 16 is preferably formed on a rear surface 27a of surgical cassette 27. Surgical cassette 27 preferably also has a top surface 27b and a bottom surface 27c. Chambers 16a and 16b are preferably separated by a divider 16c, and chambers 16a and 16b are not fluidly coupled. Dual infusion chamber 16 preferably also has an upper surface 16d and a lower surface 16e. As shown best in FIGS. 1-2, chamber 16b has an opening 226 disposed on or near lower surface 16e for fluid line 74, and chamber 16a has an opening 228 disposed on or near lower surface 16e for fluid line 72. As used in the context of the preceding sentence, "near" preferably means closer to lower surface 16e than to a transverse plane passing through a midpoint between lower surface 16e and upper surface 16d, and "near" more preferably means closer to lower surface 16e than to a transverse plane passing through a point one quarter of the distance from lower surface 16e and three quarters of the distance from upper surface 16d. Fluid level sensors 18 and 20 may be any suitable device for measuring the level of fluid in infusion chambers 16a and 16b, respectively. Fluid level sensors 18 and 20 are preferably capable of measuring the level of fluid in infusion chambers 16a and 16b in a continuous manner. Flow sensor 22 may be any suitable device for measuring the flow rate of fluid within fluid line 80. Flow sensor 22 is preferably a non-invasive flow sensor. Filters 24 and 26 are hydrophobic micro-bacterial filters. A preferred filter is the Versapor® membrane filter (0.8 micron) available from Pall Corporation of East Hills, N.Y. Microprocessor 28 is capable of implementing feedback control, and preferably PID control. Surgical device 29 may be any suitable device for providing surgical irrigating fluid to the eye but is preferably an infusion cannula, an irrigation handpiece, or and irrigation/aspiration handpiece. The portions of fluid lines 70-80 disposed in surgical cassette 27, and the portions of gas lines 84-46 disposed in surgical cassette 27, may be any suitable line, tubing, or manifold for transporting a fluid but are preferably manifolds integrally molded into surgical cassette 27.

In operation, fluid lines 70, 72, and 74; chambers 16a and 16b; fluid lines 76, 78, and 80; and surgical device 29 are all primed with a surgical irrigating fluid 140 by pressurizing infusion source 14. Surgical irrigating fluid 140 may be any surgical irrigating fluid suitable for ophthalmic use, such as, by way of example, BSS PLUS® intraocular irrigating solution available from Alcon Laboratories, Inc.

The pressurizing of infusion source 14 is preferably performed by pressure cuff 12. More specifically, microprocessor 28 sends a control signal to open solenoid valve 42 via interface 106 and to close solenoid valves 44 and 46 via interfaces 108 and 110, respectively. Microprocessor 28 also sends a control signal to open proportional solenoid valve 40 via interface 104 so that manifold 30 supplies the appropriate amount of pressurized air to actuate pressure cuff 12. Pressure transducer 68 senses the pressure within gas line 82 and provides a corresponding signal to microprocessor 28 via interface 126. Solenoid valves 48-54 are initially open so that manifold 32 provides pressurized air to actuate actuators 56-62 to close fluid lines 72-78. Microprocessor 28 sends control signals to close solenoid valves 48-54 via interfaces 114-120. The closing of solenoid valves 48-54 actuates actuators 56-62 to open fluid lines 72-78. After all chambers and fluid lines are primed, microprocessor 28 closes actuators 56-62 and thus fluid lines 72-78. Alternatively, the pressuring of infusion source 14 may be performed solely via gravity.

After priming, a user then provides a desired intraocular pressure to microprocessor 28 via an input 134. Input 134 may be any suitable input device but is preferably a touch screen display or physical knob. Chamber 16b is preferably the initial active infusion chamber. Microprocessor 28 sends appropriate control signals to open solenoid valve 44 and to open proportional solenoid valve 36 (via interface 100) to provide an appropriate level of pressurized air to chamber 16b. Pressure transducer 64 senses the pressure within gas line 84 and provides a corresponding signal to microprocessor 28 via interface 124. Microprocessor 28 also sends an appropriate control signal to open actuator 60 and thus fluid line 78. Chamber 16b supplies pressurized fluid 140 to the eye via fluid lines 78 and 80 and surgical device 29. Flow sensor 22 measures the flow rate of fluid 140 and provides a corresponding signal to microprocessor 28 via interface 132. Microprocessor 28 calculates a predicted intraocular pressure using the signal from flow sensor 22 and empirically determined impedance information of microsurgical system 10. Microprocessor 28 then sends an appropriate feedback control signal to proportional solenoid valve 36 to maintain the predicted intraocular pressure at or near the desired intraocular pressure during all portions of the surgery.

Fluid level sensor 20 continuously monitors the decrease in the level of fluid 140 in chamber 16b during surgery and provides a corresponding signal to microprocessor 28 via interface 130. Microprocessor 28 performs adjustments to the air pressure provided to chamber 16b to accommodate for the difference in fluid head height as the level of fluid 140 decreases. When the level of fluid 140 in chamber 16b reaches a bottom limit level, microprocessor 28 closes solenoid valve 44 and actuator 60 and opens solenoid valve 46 and actuators 58 and 62. Chamber 16a is now the active infusion chamber. Microprocessor 28 sends an appropriate control signal to proportional solenoid valve 38 via interface 102 to provide an appropriate level of pressurized air to chamber 16a. Pressure transducer 66 senses the pressure within gas line 86 and provides a corresponding signal to microprocessor 28 via interface 122. Chamber 16a supplies pressurized fluid 140 to the eye via fluid lines 76 and 80 and surgical device 29. Flow sensor 22 measures the flow rate of fluid 140 and provides a corresponding signal to microprocessor 28 via interface 132. Microprocessor 28 calculates the predicted intraocular pressure as described above and the sends an appropriate feedback signal to proportional solenoid valve 38 to maintain the predicted intraocular pressure at or near the desired intraocular pressure during all portions of the surgery. Microprocessor 28 closes actuator 58 and fluid line 74 once chamber 16b is refilled with fluid 140.

Fluid level sensor 18 continuously monitors the decrease in the level of fluid 140 in chamber 16a during surgery and provides a corresponding signal to microprocessor 28 via interface 128. Microprocessor 28 performs adjustments to the air pressure provided to chamber 16a to accommodate for the difference in fluid head height as the level of fluid 140 decreases. When the level of fluid 140 in chamber 16a reaches a bottom limit level, microprocessor 28 switches chamber 16b to active infusion, makes chamber 16a inactive, and refills chamber 16a with fluid 140 via fluid line 72. This cycling between chambers 16b and 16a continues throughout the surgery.

Infusion source 14 is preferably monitored via a fluid level sensor (not shown) capable of providing a signal to microprocessor 28 via interface 112 when source 14 reaches a near empty limit. Chambers 16a and 16b also preferably each have a volume that enable infusion source 14 to be exchanged, when near empty, without interrupting the surgical procedure. More specifically, chambers 16a and 16b preferably each have a volume of about 30 cc. Such volume allows about two minutes for a near empty infusion source 14 to be exchanged during conditions of maximum flow (e.g. core vitrectomy). In addition, since fluid lines 72 and 74 are fluidly coupled to chambers 16a and 16b, respectively, at or near lower surface 16e, once infusion source 14 is exchanged all air bubbles within fluid lines 70, 72, and 74 will be automatically "scrubbed out" as the inactive chamber 16a or 16b refills, without the need for re-priming.

In the case of failure of either of chambers 16a or 16b, microprocessor 28 can preferably continue surgery with only one active chamber. In the case of failure of both chambers 16a and 16b, microprocessor 28 can preferably continue surgery using only infusion source 14.

Figure 2:
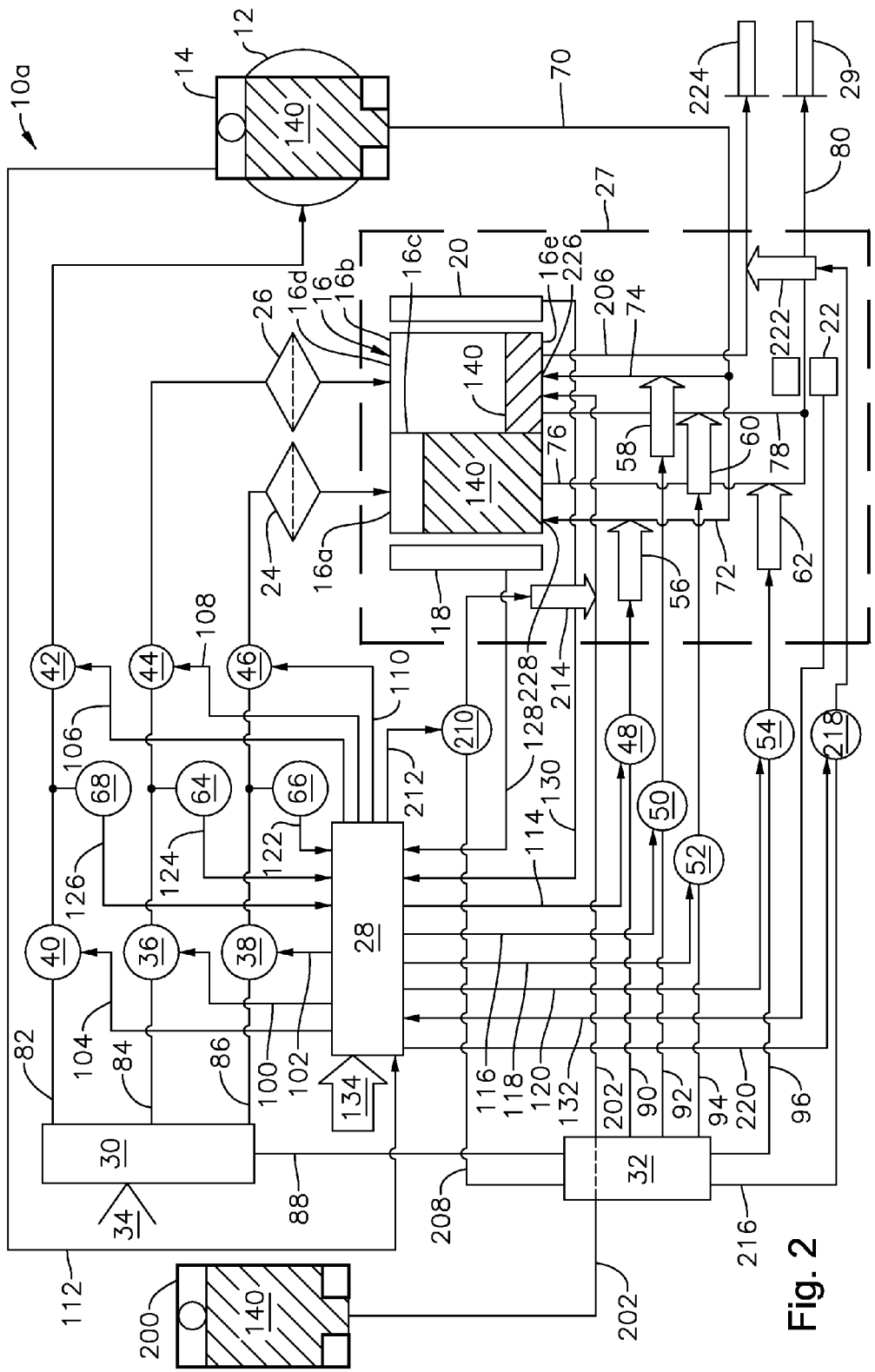
FIG. 2 is a schematic diagram illustrating infusion control and irrigation control in an ophthalmic microsurgical system.
Figure 3:
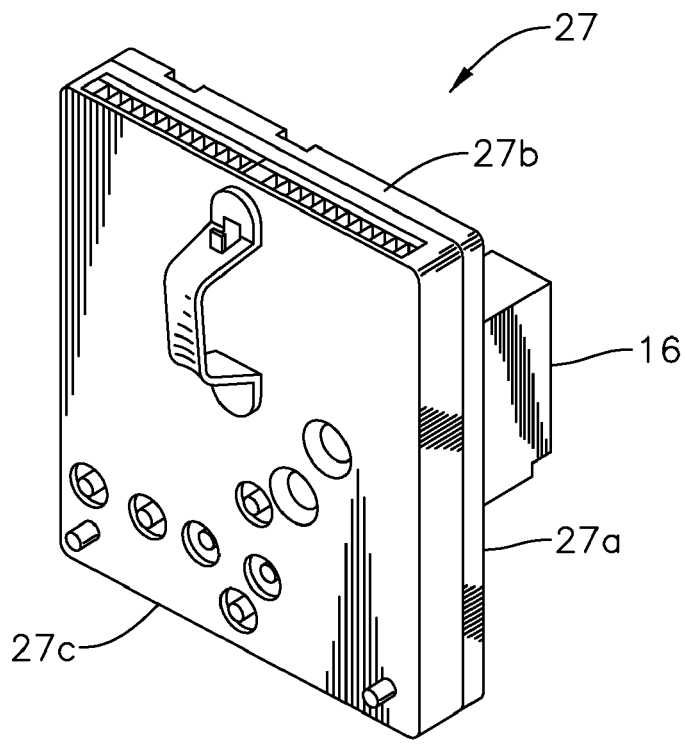
FIG. 3 is a front, perspective view of a preferred surgical cassette for use in the ophthalmic microsurgical system of FIGS. 1 and 2.
Figure 4:
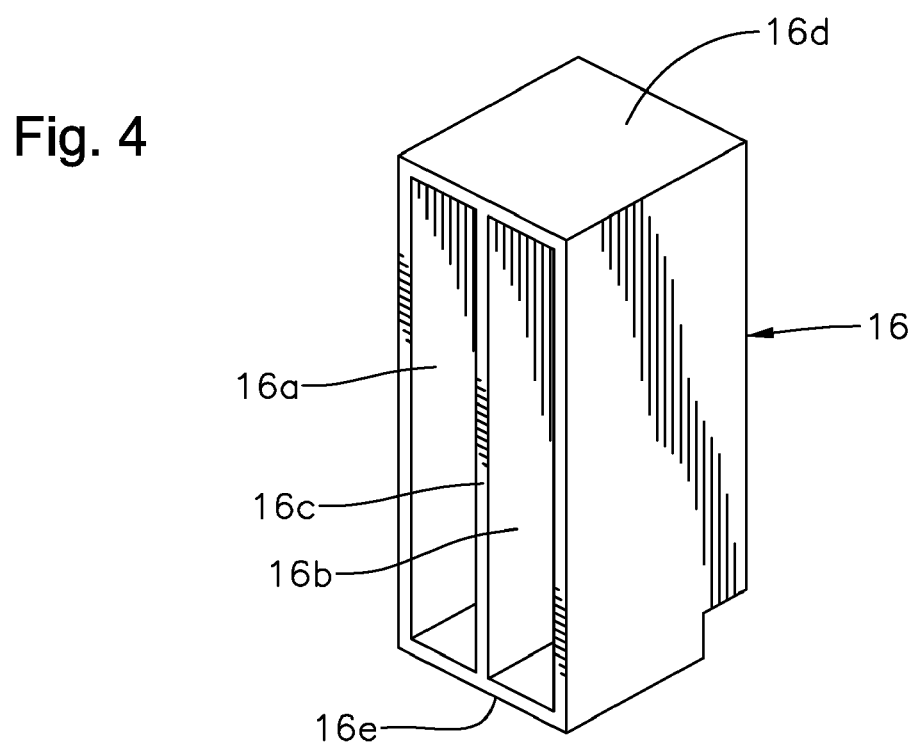
FIG. 4 is a front, perspective, partially fragmentary view of a dual infusion chamber of the surgical cassette of FIG. 3.

FIG. 2 shows a modified ophthalmic microsurgical system 10a. Microsurgical system 10a is similar to microsurgical system 10 except that it has an irrigation system in addition to the infusion system described above for system 10. More specifically, system 10a is identical to system 10 except that system 10a also includes an irrigation source 200; fluid lines 202 and 206; gas lines 208 and 216; solenoid valves 210 and 218; actuators 214 and 222; electrical interfaces 212 and 220; and a surgical device 224. As shown in FIG. 2, irrigation source 200 is pressurized solely by gravity. The portions of fluid lines 202 and 206 disposed in surgical cassette 27, and the portions of gas lines 208 and 216 disposed in surgical cassette 27, may be any suitable line, tubing, or manifold for transporting a fluid but are preferably manifolds integrally molded into surgical cassette 27. As will be appreciated by one of ordinary skill in the art, microsurgical system 10a allows surgical irrigating fluid 140 to be delivered to surgical device 29 via fluid line 80 (infusion), and surgical irrigating fluid 140 to be delivered to surgical device 224 via fluid line 206 (irrigation), independently. Microprocessor 28 can calculate flow information for fluid 140 within fluid line 206 by continuously monitoring the volumetric change of fluid inside chamber 16*b*, as indicated by fluid sensor 20.

From the above, it may be appreciated that the present invention provides an improved method of controlling intraocular pressure with a microsurgical system. The present invention is illustrated herein by example, and various modifications may be made by a person of ordinary skill in the art. For example, while the present invention is described above relative to controlling intraocular pressure in an ophthalmic microsurgical system, it is also applicable to controlling pressure within the operative tissue during other types of microsurgery.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims

What is claimed is:

1. A surgical cassette, comprising:
    a dual infusion chamber for receiving an irrigating fluid from a source external to said cassette, said dual infusion chamber disposed within an interior of said surgical cassette, said dual infusion chamber having a first chamber and a second chamber, each of said first chamber and said second chamber having a volume sufficient to hold an amount of irrigating fluid to enable said source of irrigating fluid to be exchanged without interrupting a surgical procedure, said first chamber not fluidly coupled to said second chamber;
    a first fluid line fluidly coupled to said first chamber for providing said irrigating fluid to said first chamber;
    a second fluid line fluidly coupled to said first chamber for providing said irrigating fluid to a surgical device;
    a third fluid line fluidly coupled to said second chamber for providing said irrigating fluid to said second chamber;
    a fourth fluid line fluidly coupled to said second chamber for providing said irrigating fluid to said surgical device; and
    a fifth fluid line fluidly coupled to one of said first chamber or said second chamber for providing said irrigating fluid to said one of said first chamber or said second chamber from a second source external to said cassette.

2. The surgical cassette of claim 1 further comprising a sixth fluid line fluidly coupled to said one of said first chamber or said second chamber for providing said irrigating fluid to a second surgical device.

\* \* \* \* \*